United States Patent [19]

Sills et al.

[11] Patent Number: 4,780,404

[45] Date of Patent: Oct. 25, 1988

[54] SUPERSENSITIZATION OF SILVER HALIDE EMULSION

[75] Inventors: Peter D. Sills, St. Paul; James B. Philip, Jr., Mahtomedi; Richard J. Loer, Cottage Grove; Craig Perman, Woodbury, all of Minn.

[73] Assignee: Minnesota Mining and Manufacturing Company, St. Paul, Minn.

[21] Appl. No.: 59,932

[22] Filed: Jun. 9, 1987

[51] Int. Cl.$^4$ .................................................. G03C 1/28
[52] U.S. Cl. ..................................... 430/572; 430/576
[58] Field of Search ............... 430/572, 600, 614, 611, 430/576

[56] References Cited

U.S. PATENT DOCUMENTS

| | | |
|---|---|---|
| 2,875,058 | 2/1959 | Carroll et al. . |
| 3,457,078 | 7/1969 | Riester . |
| 3,592,656 | 7/1971 | Brooks . |
| 3,615,632 | 10/1971 | Shiba et al. . |
| 4,030,927 | 6/1977 | Tani . |
| 4,105,454 | 8/1978 | Tani . |
| 4,387,158 | 6/1983 | Postle .................................. 430/565 |
| 4,596,767 | 6/1986 | Mihara et al. . |

FOREIGN PATENT DOCUMENTS 2140928 4/1984 United Kingdom .

*Primary Examiner*—Won H. Louie
*Attorney, Agent, or Firm*—Donald M. Sell; Mark A. Litman

[57] ABSTRACT

5-substituted-1,2,3,4-thiatriazoles have been found to be supersensitizers for silver halide photographic emulsions spectrally sensitized to the infrared.

19 Claims, No Drawings

SUPERSENSITIZATION OF SILVER HALIDE EMULSION

BACKGROUND OF THE INVENTION

1. Field of the Invention

This invention relates to the use of supersensitizers in photographic emulsions.

2 Background of the Art

In most uses of silver halide in photographic materials, it is desirable to increase the speed or sensitivity of the emulsion. There are a number of different techniques for increasing the speed of an emulsion which are usually classified as chemical sensitization or spectral sensitization. Chemical sensitization usually involves modification of the silver halide grains to make the most efficient use of the radiation that they absorb. The three general types of chemical sensitization are sulfur sensitization, reduction sensitization, and precious (noble) metal sensitization. These methods of chemical sensitization are well known and firmly established in the art (e.g., James, T. H. and Vanselow, W. "Chemical Sensitization", J. Photo. Sci., 1, 133 (1953), Freiser, H. and Ranz, E., Ber der Bunsengesellschaft, 68, 389 (1964), and Pouradier, J. "Chemical Sensitization", Photographic Theory: Liege Summer School, A. Hautot, p. 111, Focal Press (London 1963).

Spectral sensitization enables grains to benefit from radiation in regions of the electromagnetic spectrum where the silver halide would ordinarily not absorb. Dyes which absorb radiation and can transfer energy to the grains to help in the photoreduction of silver ions to clusters of silver metal are conventionally used to effect spectral sensitization.

Another phenomenon associated with the use of spectral sensitizing dyes is known in the art as supersensitization. The addition of other substances, frequently in quantities ranging from an equivalent molar rate to a 100 fold molar excess of supersensitizer to dye, can increase the spectrally sensitized speed of the emulsion by more than an order of magnitude. Some supersensitizers are dyes themselves, but many others do not absorb radiation in significant amounts in the visible portion of the electromagnetic spectrum. Therefore, the effect of supersensitizers on spectral sensitization is not clearly dependent on the abilty of compounds to absorb radiation in the visible portion of the spectrum. Certain cyanines, merocyanine compounds analogous to cyanines, certain acylmethylene derivatives of heterocyclic bases, and ketone derivatives such as p-dimethylaminobenzalacetone are known supersensitizers. An expanded selection of supersensitizers is therefore desired.

Mercaptotetrazoles are generally taught in U.S. Pat. Nos. 2,403,977; 3,266,897; and 3,397,987.

U.S. Pat. No. 2,875,058 describes the use of triazines such as Leucophor BCF to supersensitize infrared sensitized silver halide emulsions.

U.S. Pat. No. 4,596,767 describes the use of certain heterocyclic salts to supersensitize infrared sensitized silver halide emulsions.

Great Britain patent No. 2,140,928 shows silver halide emulsions spectrally sensitized to the infrared by quinoline dyes which are supersensitized with diazines or triazines. Dye precursors and polyethylene oxide are also used with the supersensitizer.

U.S. Pat. No. 4,030,927 and 4,105,454 describe red and infrared sensitive emulsions which are supersensitized by halogen substituted benzotriazoles and benzotriazole compounds, respectively.

U.S. Pat. No. 3,592,656 describes the supersensitization of merocyanine dye sensitized silver halide emulsions with heterocyclic compounds selected from pyrazoles, 5-pyrazolones, 3-pyrazolones, 3,5-pyrazolidenediones, triazoles, tetrazoles, xanthines, imidazoles, imidazolidines, and imidiazolinium salts.

U.S. Pat. No. 3,457,078 describes the use of mercapto substituted oxazine, oxazole, thiazole, thiadiazole, imidazole or tetrazole as supersensitizers in combination with certain cyanine dyes.

U.S. Pat. No. 3,637,393 describes the use of mercaptotetrazoles in combination with certain hydroquinone compounds to reduce fog and increase speed in photographic emulsions.

SUMMARY OF THE INVENTION

Silver halide emulsions which have been spectrally sensitized to the infrared and near infrared regions of the electromagnetic spectrum are supersensitized by the addition of 5-substituted-1,2,3,4-thiatriazoles.

DETAILED DESCRIPTION OF THE INVENTION

Silver halide crystals have an inherent photosensitivity only in the ultraviolet and blue regions of the electromagnetic spectrum. In order to provide the crystals with sensitivity to other portions of the electromagnetic spectrum, dyes are used. These dyes which extend the range of sensitivity of the silver halide are generally referred to as spectral sensitizing dyes. As noted above, supersensitizers increase the efficiency of these spectral sensitizing dyes.

Traditionally, emulsions which have been spectrally sensitized to the infrared regions of the spectrum have been sensitized inefficiently. The relative sensitivities of infrared sensitized emulsions tend to be lower than the relative sensitivities of emulsions spectrally sensitized to the visible regions of the spectrum. The need for supersensitizers in the infrared is therefore considered to be generally very important.

It has been found in the present invention that 5-substituted -1,2,3,4-thiatriazoles wherein the 5-substituent is connected through an amine linking group are effective supersensitizers for silver halide emulsions spectrally sensitized to wavelengths longer than 750 nm. Preferably the amine linking group is a secondary amine (i.e., —NH—). More preferably the supersensitizers of the present invention are represented by the structural formula

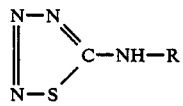

wherein R is selected from the group consisting of alkyl (preferably of 1 to 12 carbon atoms, more preferably of 1 to 4 carbon atoms), aryl (preferably phenyl and substituted phenyl, more preferably p-substituted phenyl, with examples of preferred substituents being selected from the class consisting of halogen (e.g. Br and Cl), hydroxyl, alkyl (e.g. of 1 to 12 carbon atoms, preferably 1 to 4 carbon atoms), alkoxy (e.g. of 1 to 12 carbon atoms, preferably of 1 to 4 carbon atoms), fused aromatic rings (to form naphthyl groups or substituted naphthyl groups with substituents preferred similar to those used with R equals substituted aryl)), allyl, and 5- or 6-membered heterocyclic rings composed of C, S, N, and O atoms, with at least one carbon atom. Specific examples of these compounds are 5-anilino1,2,3,4-thiatriazole (ATT), 5-(1-naphthylamino)-1,2,3,4-thiatriazole (NATT), 5-(N-ethylamino)-1,2,3,4-thiatriazole (EATT), 5-allylamino-1,2,3,4-thiatriazole (AATT), 5-(p-chloroanilino)-1,2,3,4-thiatriazole (CATT), 5-(p-methoxyanilino)-1,2,3,4-thiatriazole (PMATT), 5-methylamino-1,2,3,4-thiatriazole (MATT), 5-(p-bromoanilino)-1,2,3,4-thiatriazole (BATT), and 5-(p-hydroxyanilino)-1,2,3,4-thiatriazole (HATT).

These type of compounds are added to the optically sensitized emulsions in any of the conventional methods by which supersensitizers or other adjuvants are added to photographic emulsions. Typically the supersensitizing compounds of the present invention are added into the emulsion mixture just prior to coating, mixed well, then coated onto the photographic substrate. The compounds are added as aqueous solutions, aqueous dispersions, or organic solvent solutions (e.g., methanol) alone, or with other desirable adjuvants.

The compounds of the present invention may be added in any effective supersensitizing amount to the photographic emulsion. The concentration of ingredients and materials can vary significantly in photographic emulsions such as from 0.5 to 10 g/m² for silver. The supersensitizers may also vary significantly in concentration. A generally useful range would be from 0.001 to 1.0 percent by dry weight of the supersensitizer to the total silver halide emulsion layer. This would generally comprise about 0.01 to 10% by weight of the silver halide in the photographic emulsion layer. A more preferred range would be from 0.1 to 5% for the total supersensitizer combination by weight of the silver halide or about 0.01 to 0.5% total dry weight of the coated emulsion layer.

Any infrared spectral sensitizing dye may be used in the practice of the present invention with the supersensitizing compounds of the present invention. Useful dyes for this purpose tend to be merocyanines, cyanines and especially tricarbocyanines. Such dye sensitizers for the infrared are described for example in U.S. Pat. Nos. 3,457,078, 3,619,154, 3,682,630, 3,690,891, 3,695,888, 4,030,932 and 4,367,800. The preferred classes of compounds are the tricarbocyanines such as the 3,3'-dialkyl-thiatricarbocyanines, thiatricarbocyanines (especially with rigidized chains), selenotricarbocyanines, and enamine tricarbocyanines.

Preferred classes of dyes according to the present invention are represented by the following general formula (I) or (II):

wherein:

$R^0$ and $R^1$ can be a substituted alkyl group or a non-substituted alkyl having from 1 to 8 carbon atoms such as, for example, methyl, ethyl, propyl, butyl, amyl, benzyl, octyl, carboxymethyl, carboxyethyl, sulfopropyl, carboxypropyl, carboxybutyl, sulfoethyl, sulfoisopropyl and sulfobutyl groups;

$X^-$ is any acid anion such as, for example, chloride, bromide, iodide, perchlorate, sulfamate, thiocyanate, p-toluenesulfonate and benzenesulfonate;

$Z^0$ and $Z^1$ are independently the non-metallic atoms necessary to complete an aromatic heterocyclic nucleus chosen within those of the thiazole series, benzothiazole series, [1,2-d]-naphthothiazole series, [2,1-d]-naphthothiazole series, oxazole series, benzoxazole series, selenazole series, benzoselenazole series, [1,2-d]-naphthoselenazole series, [2,1-d]-naphthoselenazole series, thiazoline series, 4-quinoline series, 2-pyridine series, 4-pyridine series, 3,3,-dialkyl-indolenine series (wherein alkyl has a meaning known to those skilled in the art including alkyl groups having 1 to 12 carbon atoms), imidazole series and benzimidazole series.

More particularly and preferably, the present invention refers to dyes of the type above indicated in which both heterocyclic nuclei are of the benzothiazole series.

$R^2$ and $R^3$ each represent a hydrogen atom, or an alkyl group having 1 to 5 carbon atoms such as a methyl group or an ethyl group; R: represents a hydrogen atom, a halogen atom, a hydroxy group, a carboxy group, an alkyl group having 1 to 5 carbon atoms, an unsubstituted or substituted aryl group, or an acyloxy group shown by

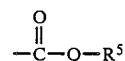

wherein $R^5$ represents an alkyl group having 1 to 5 carbon atoms, a phenyl group, or a substituted phenyl group.

Silver halide emulsions supersensitized in accordance with this invention can comprise silver chloride, silver bromide, silver bromoiodide, silver chloroiodide, silver chlorobromoiodide or mixtures thereof. Such emulsions can be coarse, medium or fine grain (or mixtures thereof) and can be prepared by any of the well-known procedures, e.g., single jet emulsions or double jet emulsions. Useful emulsions include Lippmann emulsions, ammoniacal emulsions, thiocyanate or thioether ripened emulsions such as those described in Nietz et al., U.S. Pat. No. 2,222,264, Illingsworth, U.S. Pat. No. 3,320,069, and McBride, U.S. Pat. No. 3,271,157; or cubic grain emulsions, such as those described by Kline

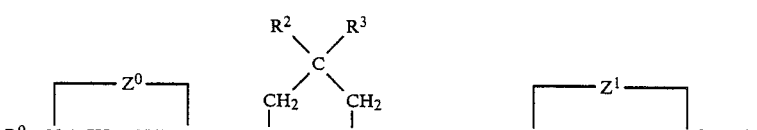

I

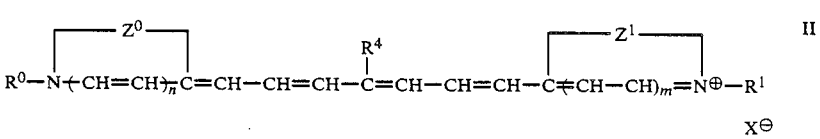

II and Moisar, Journal of Photographic Science, volume 12, page 242 et seq. or Markocki, The Spectral Sensitization of Silver Bromide Emulsions on Different Crystallographic Faces, Journal of Photographic Science, Volume 13, 1965; or Illingsworth, British patent No. 1,156,193 published June 25, 1969.

Tabular or lamellar grain emulsions as described in U.S. Pat. Nos. 4,425,425, 4,439,520 and 4,425,426 are also equally useful.

The silver halide emulsions supersensitized with the compounds of this invention can be unwashed or washed to remove soluble salts. In the latter case the soluble salts can be removed by chill-setting and leeching or the emulsion can be coagulation washed e.g., by the procedures described in Hewitson et al., U.S. Pat. No. 2,618,556; Yutzy et al., U.S. Pat. No. 2,614,928; Yackel, U.S. Pat. No. 2,565,418; Hart et al., U.S. Pat. No. 3,241,969; and Waller et al., U.S. Pat. No. 2,489,341.

Photographic emulsions containing supersensitizing combinations in accordance with this invention can be sensitized with chemical sensitizers, such as with reducing agents; sulfur, selenium or tellurium compounds; gold, platinum or palladium compounds; or combinations of these. Suitable chemical sensitization procedures are described in Shepard, U.S. Pat. No. 1,623,499; Waller, U.S. Pat. No. 2,399,083; McVeigh, U.S. Pat. No. 3,297,447; and Dunn, U.S. Pat. No. 3,297,446.

The supersensitized silver halide emulsions of this invention can contain speed increasing compounds such as polyalkylene glycols, cationic surface active agents and thioethers or combinations of these as described in Piper, U.S. Pat. No. 2,886,437; Chechak, U.S. Pat. No. 3,046,134; Carroll et al., U.S. Pat. No. 2,944,900; and Goffe, U.S. Pat. No. 3,294,540.

Silver halide emulsions containing the supersensitizing combinations of this invention can be protected against the production of fog and can be stabilized against loss of sensitivity during keeping. Suitable antifoggants and stabilizers which can be used alone or in combination, include the thiazolium salts described in Staud, U.S. Pat. No. 2,131,038 and Allen, U.S. Pat. No. 2,694,716; the azaindenes described in Piper, U.S. Pat. No. 2,886,437 and Heimbach, U.S. Pat. No. 2,444,605; the mercury salts described in Allen, U.S. Pat. No. 2,728,663; the urazoles described in Anderson, U.S. Pat. No. 3,287,135; the sulfocatechols described in Kennard, U.S. Pat. No. 3,235,652; the oximes described in Carroll et al., British patent No. 623,448; nitron; nitroindazoles, the polyvalent metal salts described in Jones, U.S. Pat. No. 2,839,405; the thiuronium salts described in Herz, U.S. Pat. No. 3,220,839; and the palladium, platinum and gold salts described in Trivelli, U.S. Pat. No. 2,566,263 and Damschroder, U.S. Pat. No. 2,597,915.

Photographic elements including emulsions supersensitized in accordance with this invention can contain incorporated developing agents such as hydroquinones, catechols, aminophenols, 3-pyrazolidones, ascorbic acid and its derivatives, reductones and phenylenediamines, or combinations of developing agents. The developing agents can be in the silver halide emulsion and/or in another suitable location in the photographic element. The developing agents can be added from suitable solvents or in the form of dispersions as described in Yackel, U.S. Pat. No. 2,592,368 and Dunn et al., French patent No. 1,505,778.

Silver halide supersensitized in accordance with the invention can be dispersed in colloids that can be hardened by various organic or inorganic hardeners, alone or in combination, such as the aldehydes, blocked aldehydes, ketones, carboxylic and carbonic acid derivatives, sulfonate esters, sulfonyl halides and vinyl sulfones, active halogen compounds, epoxy compounds, aziridines, active olefins, isocyanates, carbodiimides, mixed function hardeners and polymeric hardeners such as oxidized polysaccharides, e.g., dialdehyde starch, oxyguargum, etc.

Photographic emulsions supersensitized with the materials described herein can contain various colloids alone or in combination as vehicles or binding agents. Suitable hydrophilic materials include both naturally-occurring substances such as proteins, for example, gelatin, gelatin derivatives (e.g., phthalated gelatin), cellulose derivatives, polysaccharides such as dextran, gum arabic and the like; and synthetic polymeric substances such as water soluble polyvinyl compounds, e.g., poly(vinylpyrrolidone) acrylamide polymers or other synthetic polymeric compounds such as dispersed vinyl compounds in latex form, and particularly those which increase the dimensional stability of the photographic materials. Suitable synthetic polymers include those described, for example, in U.S. Pat. Nos. 3,142,568 of Nottorf; 3,193,386 of White; 3,062,674 or Houck, Smith and Yudelson; 3,220,844 of Houck, Smith and Yudelson; Ream and Fowler, 3,287,289; and Dykstra, U.S. Pat. No. 3,411,911; particularly effective are those water-insoluble polymers of alkyl acrylates and methacrylates, acrylic acid, sulfoalkyl acrylates or methacrylates, those which have cross linking sites which facilitate hardening or curing and those having recurring sulfobetaine units as described in Canadian patent No. 774,054.

Emulsions supersensitized in accordance with this invention can be used in photographic elements which contain antistatic or conducting layers, such as layers that comprise soluble salts, e.g., chlorides, nitrates, etc., evaporated metal layers, ionic polymers such as those described in Minsk, U.S. Pat. Nos. 2,861,056 and 3,206,312 or insoluble inorganic salts such as those described in Trevoy, U.S. Pat. No. 3,428,451.

Photographic emulsions containing the supersensitizing combinations of the invention can be coated on a wide variety of supports. Typical supports include polyester film, subbed polyester film, poly(ethylene terephthalate) film, cellulose nitrate film, cellulose ester film, poly(vinyl acetal) film, polycarbonate film and related films or resinous materials, as well as glass, paper, metal and the like. Typically, a flexible supoprt is employed, especially a paper support, which can be partially acetylated or coated with baryta and/or an alpha-olefin polymer, particularly a polymer of an alpha-olefin containing 2 to 10 carbon atoms such as polyethylene, polypropylene, ethylenebutene copolymers and the like.

Supersensitized emulsions of the invention can contain plasticizers and lubricants such as polyalcohols, e.g., glycerin and diols of the type described in Milton, U.S. Pat. No. 2,960,404; fatty acids or esters such as those described in Robijns, U.S. Pat. No. 2,588,765 and Duane, U.S. Pat. No. 3,121,060; and silicone resins such as those described in DuPont British patent No. 955,061.

The photographic emulsions supersensitized as described herein can contain surfactants such as saponin, anionic, compounds, such as the alkylarylsulfonates described in Baldsiefen, U.S. Pat. No. 2,600,831 fluorinated surfactants, and amphoteric compounds such as those described in Ben-Ezra, U.S. Pat. No. 3,133,816.

Photographic elements containing emulsion layers sensitized as described herein can contain matting agents such as starch, titanium dioxide, zinc oxide, silica, polymeric beads including beads of the type described in Jelley et al., U.S. Pat. No. 2,992,101 and Lynn, U.S. Pat. No. 2,701,245.

Spectrally sensitized emulsions of the invention can be utilized in photographic elements which contain brightening agents including stilbene, triazine, oxazole and coumarin brightening agents. Water soluble brightening agents can be used such as those described in Albers et al., German patent No. 972,067 and McFall et al., U.S. Pat. No. 2,933,390 or dispersions of brighteners can be used such as those described in Jansen, German patent No. 1,150,274 and Oetiker et al., U.S. Pat. No. 3,406,070.

Photographic elements containing emulsion layers supersensitized according to the present invention can be used in photographic elements which contain light absorbing materials and filter dyes such as those described in Sawdey, U.S. Pat. No. 3,253,921; Gaspar, U.S. Pat. No. 2,274,782; Carroll et al., U.S. Pat. No. 2,527,583 and Van Campen, U.S. Pat. No. 2,956,879. If desired, the dyes can be mordanted, for example, as described in Milton and Jones, U.S. Pat. No. 3,282,699.

The sensitizing dyes and/or supersensitizers (and other emulsion addenda) can be added to the photographic emulsions from water solutions or suitable organic solvent solutions, for example with the procedure described in Collins et al., U.S. Pat. No. 2,912,343; Owens et al., U.S. Pat. No. 3,342,605; Audran, U.S. Pat. No. 2,996,287 or Johnson et al., U.S. Pat. No. 3,425,835. The dyes can be dissolved separately or together, and the separate or combined solutions can be added to a silver halide emulsion, or a silver halide emulsion layer can be bathed in the solution of supersensitizers and/or dyes.

Contrast enhancing additives such as hydrazines, rhodium, iridium and combinations thereof are also useful.

Photographic emulsions of this invention can be coated by various coating procedures including dip coating, air knife coating, curtain coating, or extrusion coating using hoppers of the type described in Beguin, U.S. Pat. No. 2,681,294. If desired, two or more layers may be coated simultaneously by the procedures described in Russell, U.S. Pat. Nos. 2,761,791 and Wynn, British patent No. 837,095.

Silver halide emulsions containing the supersensitizer combinations of this invention can be used in elements designed for color photography, for example, elements containing color-forming couplers such as those described in Frolich et al., U.S. Pat. No. 2,376,679; Vittum et al., U.S. Pat. No. 2,322,027; Fierke et al., U.S. Pat. No. 2,801,171; Godowsky, U.S. Pat. No. 2,698,794; Barr et al., U.S. Pat. No. 3,227,554 and Graham, U.S. Pat. No. 3,046,129; or elements to be developed in solutions containing color-forming couplers such a those described in Mannes and Godowsky, U.S. Pat. No. 2,252,718; Carroll et al. U.S. Pat. No. 2,592,243 and Schwan, U.S. Pat. No. 2,950,970.

Exposed photographic emulsions of this invention can be processed by various methods including processing in alkaline solutions containing conventional developing agents such as hydroquinones, catechols, aminophenols, 3-pyrazolidones, phenylenediamines, ascorbic acid derivatives, hydroxylamines, hydrazines and the like; web processing such as described in Tegillus et al., U.S. Pat. No. 3,179,517; stabilization processing as described in Yackel et al. "Stabilization Processing of Films and Papers", PSA Journal, Vol. 16B, August 1950; monobath processing as described in Levy "Combined Development and Fixation of Photographic Images with Monobaths", Phot. Sci. and Eng., Vol. 2, No. 3, October 1958, and Barnes et al., U.S. Pat. No. 3,392,019. If desired, the photographic emulsions of this invention can be processed in hardening developers such as those described in Allen et al., U.S. Pat. No. 3,232,761; in a roller transport processor such as those described in Russell, U.S. Pat. No. 3,025,779; or by surface application processing as described in Example 3, of Kitze, U.S. Pat. No. 3,418,132.

The following is the description of a general synthetic procedure which may be used in the preparation of any 5-substituted-1,2,3,4-thiatriazole.

Preparation of Aryl Thiosemicrabazides

To a cooled and stirred ethanolic solution of the primary aromatic amine (0.25 mole) having the selected R group was slowly added 40 mls of ammonium hydroxide (sp. gr. 0.90). With the temperature maintained below 20° C., carbon disulfide (15 mls) was added over a 15 minute period. After one hour, an aqueous solution of the sodium salt of monochloroacetic acid (0.25 mole) was added to this mixture followed by addition of hydrazine hydrate (0.25 mole). The mixture was cooled overnight in a refrigerator. The crude thiosemicarbazide was filtered out and recrystallized from ethanol and water.

Preparation of 5-Amino Substituted 1,2,3,4-Thiatriazole

To a cooled and stirred mixture of the thiosemicarbazide (0.10 mole) generated in the above procedure and hydrochloric acid (76.0 ml, 15%) was added sodium nitrite (0.10 mole, 6.90 grams) in 50 mls of water over a period of 30 minutes. The solid material which formed was filtered and recrystallized from ethanol. Melting points, where available, were in agreement with values reported in the literature. NMR and IR spectral data correlated with the appropriate structures.

These and other aspects of the invention will be shown by the Examples.

Two different emulsions are used in the various examples to show the practice of the present invention. Emulsion A was prepared by a double jet precipitation to provide an emulsion with 64% chloride and 36% bromide with an average grain size of 0.24 micrometers. The emulsion was divided in half for two different types of chemical sensitization. Emulsion Aa was digested with sodium thiosulfate while Ab was digested with p-toluenesulfinic acid, sodium thiosulfate and sodium gold tetrachloride ($NaAuCl_4$).

Emulsion B is an ammoniacal iodobromide emulsion made by double jet precipitation with all potassium iodide and ammonia in the kettle before precipitation. The resulting emulsion was 3% iodide and 97% bromide with an average grain size of 0.24 micrometers. The emulsion was then chemically digested with sulfur and gold.

Final preparation of the emulsions comprised the addition of water and gelatin to a level of 5.0% gelatin and 2500 g of emulsion per mole of silver. The pH was adjusted to 7.0, and the pAg was adjusted to 7.2. Infrared sensitizing dyes were added as 0.04% by weight solutions in methanol. The thiatriazoles were added as a 0.1% methanol solution and poly(ethylacrylate) (hereinafter PEA) as a 20% aqueous dispersion. Formaldehyde hardener and any other indicated materials were added before coating as an aqueous solution.

and the percent that change (dS) represented (% dS). The amounts of PMT, and thiatriazole are presented in grams per mole of silver. The results are shown in Tables IA and IB for emulsion Ab. The coating weight was 2.2 g of silver per square meter. PMT is phenylmercaptotetrazole.

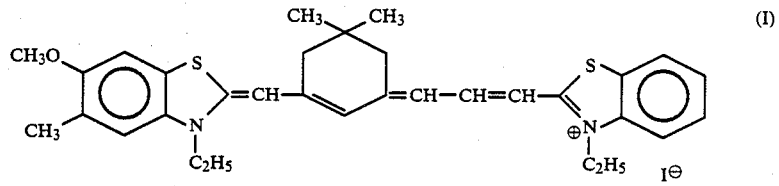
(I)

TABLE IA

| Ex. | Name | Qty. | PEA | Dmin | Dmax | S | C | dS | % dS |
|---|---|---|---|---|---|---|---|---|---|
| A | — | — | 0 | 0.050 | 2.59 | 1.50 | 2.48 | — | 100 |
| B | — | — | 30 | 0.145 | 2.81 | 1.68 | 2.55 | 0.18 | 151 |
| C | PMT | 0.115 | 30 | 0.142 | 3.13 | 2.18 | 2.65 | 0.68 | 479 |
| 1 | ATT | 0.150 | 30 | 0.141 | 3.14 | 2.20 | 2.62 | 0.70 | 501 |
| 2 | HATT | 0.050 | 30 | 0.142 | 2.99 | 1.87 | 2.62 | 0.37 | 234 |
| 3 | HATT | 0.100 | 30 | 0.140 | 3.07 | 1.98 | 2.66 | 0.48 | 302 |
| 4 | HATT | 0.150 | 30 | 0.144 | 3.13 | 2.05 | 2.66 | 0.55 | 355 |
| 5 | HATT | 0.200 | 30 | 0.141 | 3.12 | 2.04 | 2.63 | 0.54 | 347 |
| 6 | NATT | 0.050 | 30 | 0.149 | 3.12 | 2.06 | 2.55 | 0.56 | 363 |
| 7 | NATT | 0.100 | 30 | 0.142 | 3.12 | 2.16 | 2.45 | 0.66 | 457 |
| 8 | NATT | 0.150 | 30 | 0.146 | 3.07 | 2.12 | 2.40 | 0.62 | 417 |

EXAMPLES 1-34

The effect of the thiatriazole supersensitizing additives on photographic silver halide emulsions were investigated. Emulsion Ab (the sulfur and gold digested chlorobromide emulsion) was dyed with the infrared sensitizing dye (I) shown below. The coated and dried film was aged one week before exposing on a sensitometer for $10^{-3}$ seconds through an 820 nm narrow band filter. The exposed films were developed in a 90 second X-ray processor. Sensitometric results included $D_{min}$, $D_{max}$, speed (at O.D.=1.0), average contrast (C), change in speed from emulsion without additives (dS), The above examples were coated on blue polyester base resulting in high $D_{min}$ values except for Example A which was on clear polyester. However, the blue base has no effect upon the speed of the system. All other examples were coated on a clear 7 mil ($1.78 \times 10^{-4}$ m) polyester.

TABLE IB

| Ex. | Name | Qty. | PEA | Dmin | Dmax | S | C | dS | % dS |
|---|---|---|---|---|---|---|---|---|---|
| D | — | — | 0 | 0.050 | 2.59 | 1.50 | 2.48 | — | 100 |
| E | — | — | 30 | 0.043 | 2.71 | 1.69 | 2.41 | 0.19 | 155 |
| F | PMT | 0.115 | 30 | 0.041 | 3.00 | 2.22 | 2.48 | 0.72 | 524 |
| 9 | ATT | 0.100 | 30 | 0.040 | 3.00 | 2.22 | 2.54 | 0.72 | 524 |
| 10 | ATT | 0.150 | 30 | 0.042 | 3.06 | 2.27 | 2.50 | 0.77 | 589 |
| 11 | ATT | 0.200 | 30 | 0.041 | 3.10 | 2.23 | 2.49 | 0.73 | 537 |
| 12 | NATT | 0.100 | 30 | 0.046 | 2.93 | 2.20 | 2.44 | 0.70 | 501 |
| 13 | EATT | 0.100 | 30 | 0.047 | 2.94 | 2.02 | 2.75 | 0.52 | 331 |
| 14 | EATT | 0.150 | 30 | 0.047 | 2.97 | 2.06 | 2.71 | 0.56 | 363 |
| 15 | EATT | 0.200 | 30 | 0.047 | 2.90 | 2.04 | 2.63 | 0.54 | 347 |
| 16 | AATT | 0.050 | 30 | 0.048 | 2.94 | 2.00 | 2.64 | 0.50 | 316 |
| 17 | AATT | 0.100 | 30 | 0.048 | 3.11 | 2.12 | 2.76 | 0.62 | 417 |
| 18 | AATT | 0.150 | 30 | 0.047 | 3.04 | 2.11 | 2.73 | 0.61 | 407 |
| 19 | CATT | 0.050 | 30 | 0.050 | 3.31 | 2.18 | 2.66 | 0.68 | 479 |
| 20 | CATT | 0.100 | 30 | 0.049 | 2.98 | 2.32 | 2.52 | 0.82 | 661 |
| 21 | CATT | 0.150 | 30 | 0.047 | 3.11 | 2.36 | 2.59 | 0.86 | 724 |
| 22 | CATT | 0.200 | 30 | 0.047 | 2.99 | 2.32 | 2.69 | 0.82 | 661 |
| 23 | PMATT | 0.050 | 30 | 0.050 | 2.98 | 2.04 | 2.54 | 0.54 | 347 |
| 24 | PMATT | 0.100 | 30 | 0.050 | 3.01 | 2.21 | 2.54 | 0.71 | 513 |
| 25 | PMATT | 0.150 | 30 | 0.049 | 2.98 | 2.26 | 2.49 | 0.76 | 575 |
| 26 | PMATT | 0.200 | 30 | 0.048 | 3.15 | 2.29 | 2.56 | 0.79 | 616 |
| 27 | MATT | 0.050 | 30 | 0.048 | 2.72 | 1.87 | 2.44 | 0.37 | 234 |
| 28 | MATT | 0.100 | 30 | 0.050 | 2.92 | 1.91 | 2.53 | 0.41 | 257 |
| 29 | MATT | 0.150 | 30 | 0.049 | 2.73 | 1.81 | 2.40 | 0.31 | 204 |
| 30 | MATT | 0.200 | 30 | 0.050 | 2.81 | 1.76 | 2.45 | 0.26 | 182 |
| 31 | BATT | 0.050 | 30 | 0.048 | 2.58 | 1.97 | 2.18 | 0.47 | 295 |
| 32 | BATT | 0.100 | 30 | 0.047 | 2.88 | 2.05 | 2.48 | 0.55 | 355 |
| 33 | BATT | 0.150 | 30 | 0.047 | 2.93 | 2.11 | 2.50 | 0.61 | 407 |
| 34 | BATT | 0.200 | 30 | 0.046 | 2.93 | 2.08 | 2.54 | 0.58 | 380 |

EXAMPLES 35-40

An additional experiment was performed to separate the effects of PEA from ATT and PMT. Emulsion Ab(the sulfur and gold digested chlorobromide emulsion) was dyed with infrared sensitizing dye (DYE 1). The emulsion was coated at 2.4 g Ag/m². Sensitometric evaluation was also run on samples incubated under the extreme conditions of 7 days at 50° C. and 60% R.H. The results are reported in Table II.

TABLE II

| | Additive | | | Fresh | | | | | | Incubated 7 Days | | | | |
|---|---|---|---|---|---|---|---|---|---|---|---|---|---|---|
| Ex. | PEA | PMT | ATT | Dmin | Dmax | S | C | dS | % dS | Dmin | Dmax | S | C | -dS |
| G | 0 | 0 | 0 | 0.050 | 3.30 | 1.47 | 2.68 | — | 100 | 0.076 | 3.02 | 1.40 | 2.17 | 0.07 |
| H | 30 | 0 | 0 | 0.051 | 3.26 | 1.65 | 2.76 | 0.18 | 151 | 0.080 | 3.06 | 1.57 | 2.19 | 0.08 |
| I | 0 | 0.115 | 0 | 0.049 | 3.29 | 2.15 | 2.89 | 0.68 | 479 | 0.058 | 3.13 | 2.03 | 2.45 | 0.12 |
| J | 30 | 0.115 | 0 | 0.050 | 3.20 | 2.22 | 2.82 | 0.75 | 562 | 0.064 | 3.13 | 2.10 | 2.45 | 0.12 |
| 35 | 0 | 0 | 0.10 | 0.055 | 3.36 | 2.16 | 2.87 | 0.69 | 490 | 0.067 | 3.21 | 2.03 | 2.46 | 0.13 |
| 36 | 30 | 0 | 0.10 | 0.050 | 3.32 | 2.21 | 2.85 | 0.74 | 550 | 0.064 | 3.13 | 2.10 | 2.44 | 0.11 |
| 37 | 0 | 0 | 0.15 | 0.056 | 3.38 | 2.19 | 2.87 | 0.72 | 525 | 0.063 | 3.24 | 2.08 | 2.50 | 0.11 |
| 38 | 30 | 0 | 0.15 | 0.051 | 3.24 | 2.23 | 2.81 | 0.76 | 575 | 0.059 | 3.16 | 2.15 | 2.47 | 0.08 |
| 39 | 0 | 0 | 0.20 | 0.057 | 3.45 | 2.19 | 2.85 | 0.72 | 525 | 0.062 | 3.20 | 2.07 | 2.47 | 0.12 |
| 40 | 30 | 0 | 0.20 | 0.049 | 3.28 | 2.18 | 2.75 | 0.71 | 513 | 0.056 | 3.06 | 2.09 | 2.43 | 0.09 |

The best overall system incorporates ATT as the supersensitizer. Additional improvements in fresh and incubated sensitometry are obtained by combining PEA with ATT as in Example 38 which has low $D_{min}$ and high speed and only a small fog increase and speed loss after 7 days at 50° C.

EXAMPLES 41-44

The supersensitization effects of ATT and NATT were evaluated with the sulfur digested chlorobromide emulsion (Aa) and an infrared dye (DYE 1) coated at 2.7 g Ag./m². The results are reported in Table III and clearly show supersensitization.

TABLE III

| | Additives | | | Fresh | | | | | |
|---|---|---|---|---|---|---|---|---|---|
| Ex. | ATT | NATT | PEA | Dmin | Dmax | S | C | dS | % dS |
| K | 0 | 0 | 0 | 0.057 | 3.74 | 1.35 | 1.87 | — | 100 |
| L | 0 | 0 | 30 | 0.056 | 3.85 | 1.50 | 1.93 | 0.15 | 141 |
| 41 | 0.15 | 0 | 0 | 0.051 | 4.15 | 1.77 | 2.07 | 0.42 | 263 |
| 42 | 0.15 | 0 | 30 | 0.050 | 3.90 | 1.81 | 2.03 | 0.46 | 288 |
| 43 | 0 | 0.10 | 0 | 0.053 | 4.07 | 1.82 | 1.99 | 0.47 | 295 |
| 44 | 0 | 0.10 | 30 | 0.052 | 3.80 | 1.81 | 1.85 | 0.46 | 288 |

EXAMPLES 45-48

The effects of ATT and NATT were determined with the sulfur and gold digested iodobromide emulsion (Emulsion B). The test emulsion was sensitized with DYE 1 and coated at 2.4 g Ag/m². The results are reported in Table IV and are clear examples of supersensitization.

TABLE IV

| | Additives | | | Fresh | | | | | |
|---|---|---|---|---|---|---|---|---|---|
| Ex. | ATT | NATT | PEA | Dmin | Dmax | S | C | dS | % dS |
| M | 0 | 0 | 0 | 0.069 | 3.58 | 1.51 | 2.05 | — | 100 |
| N | 0 | 0 | 30 | 0.070 | 3.36 | 1.56 | 1.99 | 0.05 | 112 |
| 45 | 0.15 | 0 | 0 | 0.064 | 3.45 | 1.99 | 2.08 | 0.48 | 302 |
| 46 | 0.15 | 0 | 30 | 0.062 | 3.40 | 1.95 | 2.09 | 0.44 | 275 |
| 47 | 0 | 0.10 | 0 | 0.063 | 3.60 | 1.87 | 1.99 | 0.36 | 229 |
| 48 | 0 | 0.10 | 30 | 0.059 | 3.40 | 1.88 | 1.98 | 0.37 | 234 |

EXAMPLES 49-52

Examples 41-44 were repeated on emulsion Ab, the sulfur and gold digested, chlorobromide emulsion, except that the infrared sensitizing dye:

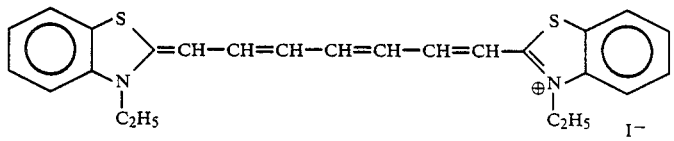

was added to the emulsion at 20 mg/mole Ag and coated at 2.25 g Ag/m². The results are reported in Table V.

TABLE V

| | Additives | | | Fresh | | | | | |
|---|---|---|---|---|---|---|---|---|---|
| Ex. | ATT | NATT | PEA | Dmin | Dmax | S | C | dS | % dS |
| O | 0 | 0 | 0 | 0.054 | 3.18 | 1.23 | 2.52 | — | 100 |
| P | 0 | 0 | 30 | 0.048 | 3.10 | 1.57 | 2.60 | 0.34 | 219 |
| 49 | 0.15 | 0 | 0 | 0.051 | 3.22 | 2.12 | 2.69 | 0.89 | 775 |
| 50 | 0.15 | 0 | 30 | 0.044 | 3.04 | 2.13 | 2.61 | 0.90 | 794 |
| 51 | 0 | 0.10 | 0 | 0.052 | 3.23 | 2.02 | 2.65 | 0.79 | 616 |

TABLE V-continued

| | Additives | | | Fresh | | | | | |
|---|---|---|---|---|---|---|---|---|---|
| Ex. | ATT | NATT | PEA | Dmin | Dmax | S | C | dS | % dS |
| 52 | 0 | 0.10 | 30 | 0.045 | 3.04 | 2.02 | 2.55 | 0.79 | 616 |

The tabulated results show that supersensitization by thiatriazoles is not limited to a particular infrared sensitizing dye.

EXAMPLES 53–56

Examples 41–44 were repeated on emulsion Ab, the sulfur and gold digested, chlorobromide emulsion, except that the infrared sensitizing dye:

was added at 30 mg/mole Ag. The emulsion was coated at 2.25 g Ag/m², and the results are reported in Table VI and clearly show supersensitization.

TABLE VI

| | Additives | | | Fresh | | | | | |
|---|---|---|---|---|---|---|---|---|---|
| Ex. | ATT | NATT | PEA | Dmin | Dmax | S | C | dS | % dS |
| Q | 0 | 0 | 0 | 0.054 | 3.20 | 0.75 | 2.60 | — | 100 |
| R | 0 | 0 | 30 | 0.051 | 3.15 | 1.05 | 2.57 | 0.30 | 200 |
| 53 | 0.15 | 0 | 0 | 0.046 | 3.25 | 1.44 | 2.56 | 0.69 | 490 |
| 54 | 0.15 | 0 | 30 | 0.043 | 3.15 | 1.48 | 2.52 | 0.73 | 537 |
| 55 | 0 | 0.10 | 0 | 0.048 | 3.22 | 1.38 | 2.40 | 0.63 | 427 |
| 56 | 0 | 0.10 | 30 | 0.045 | 3.15 | 1.44 | 2.40 | 0.69 | 490 |

What is claimed is:

1. A silver halide photographic emulsion in a hydrophilic colloidal binder, said emulsion being spectrally sensitized to the infrared portion of the electromagnetic spectrum and having a supersensitizing amount of a 5-substituted-1,2,3,4-thiatriazole wherein the 5-substituent of said 5-substituted-1, 2, 3, 4-thiatriazole is bonded to said thiatriazole through an amine group.

2. The emulsion of claim 1 wherein said amine group is a secondary amine group.

3. The emulsion of claim 1 wherein said 5-substituted-1,2,3,4-thiatriazole is represented by the general formula $$\begin{array}{c} N-N \\ \| \quad \diagdown \\ \quad \quad C-NH-R \\ \| \quad \diagup \\ N-S \end{array}$$

wherein R is selected from the group consisting of alkyl groups, aryl groups, allyl, and 5- or 6-membered heterocyclic groups having only C, N, S or O ring atoms.

4. The emulsion of claim 3 wherein R is a phenyl group.

5. The emulsion of claim 3 wherein R is an alkyl group.

6. The emulsion of claim 3 wherein R is alkyl.

7. The emulsion of claim 3 wherein poly(ethylacrylate) is also present in a supersensitizing amount.

8. The emulsion of claim 4 wherein poly(ethylacrylate) is also present in a supersensitizing amount.

9. The emulsion of claim 5 wherein poly(ethylacrylate) is also present in a supersensitizing amount.

10. The emulsion of claim 6 wherein poly(ethylacrylate) is also present in a supersensitizing amount.

11. The emulsion of claim 4 wherein said phenyl group comprises a para-substituted phenyl group.

12. The emulsion of claim 11 wherein said phenyl group has a para-substituent selected from the class consisting of halogen, alkyl, alkoxy, and hydroxy.

13. The emulsion of claim 8 wherein said phenyl group has a para-substituent selected from the class consisting of halogen, alkyl, alkoxy, and hydroxy.

14. The element of claim 1 wherein said emulsion is sensitized by a dye selected from the class consisting of thia-, benzothia-, seleno-, benzoseleno-, imida-, benzoimida-, oxa-, benzoxa-, and enamine tricarbocyanines.

15. The element of claim 2 wherein said emulsion is sensitized by a dye selected from the class consisting of thia-, benzothia-, seleno-, benzoseleno-, imida-, benzoimida-, oxa-, benzoxa-, and enamine tricarbocyanines.

16. The element of claim 3 wherein said emulsion is sensitized by a dye selected from the class consisting of thia-, benzothia-, seleno-, benzoseleno-, imida-, benzoimida-, oxa-, benzoxa-, and enamine tricarbocyanines.

17. The element of claim 4 wherein said emulsion is sensitized by a dye selected from the class consisting of thia-, benzothia-, seleno-, benzoseleno-, imida-, benzoimida-, oxa-, benzoxa-, and enamine tricarbocyanines.

18. The element of claim 8 wherein said emulsion is sensitized by a dye selected from the class consisting of thia-, benzothia-, seleno-, benzoseleno-, imida-, benzoimida-, oxa-, benzoxa-, and enamine tricarbocyanines.

19. The element of claim 12 wherein said emulsion is sensitized by a dye selected from the glass consisting of thia-, benzothia-, seleno-, benzoseleno-, imida-, benzoimida-, oxa-, benzoxa-, and enamine tricarbocyanines.

* * * * *

UNITED STATES PATENT AND TRADEMARK OFFICE
CERTIFICATE OF CORRECTION

PATENT NO. : 4,780,404
DATED : October 25, 1988
INVENTOR(S) : Sills, Philip, Loer and Perman It is certified that error appears in the above-identified patent and that said Letters Patent is hereby corrected as shown below:

Column 4, line 28 "R:" should be $--R^4--$.

Signed and Sealed this

Second Day of January, 1990

Attest:

JEFFREY M. SAMUELS

Attesting Officer   Acting Commissioner of Patents and Trademarks